United States Patent [19]

Viikari et al.

[11] Patent Number: 5,814,515
[45] Date of Patent: Sep. 29, 1998

[54] METHOD OF DISSOLUTION OF SAUSAGE SKINS AND OTHER CELLULOSIC SUBSTANCES BY MEANS OF AN ENZYME SOLUTION

[75] Inventors: Liisa Viikari, Helsinki; Annikka Mustranta, Espoo; Osmo Ojamo, Lohja; Merja Itävaara, Kirkkonummi; Tor Johansson, Tammisaari, all of Finland

[73] Assignee: Eriksson Capital AB, Finland

[21] Appl. No.: 576,826

[22] Filed: Dec. 21, 1995

[30] Foreign Application Priority Data

Dec. 23, 1994 [FI] Finland .................................. 946053

[51] Int. Cl.$^6$ ............................ C07G 17/00; A23G 1/00
[52] U.S. Cl. .................. 435/267; 435/277; 426/105; 426/138; 426/442
[58] Field of Search .................... 426/105, 138, 426/442; 435/267, 277

[56] References Cited

U.S. PATENT DOCUMENTS

| | | | |
|---|---|---|---|
| 4,529,634 | 7/1985 | Hammer et al. | 428/36 |
| 5,236,726 | 8/1993 | Lancaster | 426/135 |
| 5,348,871 | 9/1994 | Scott et al. | 435/165 |

FOREIGN PATENT DOCUMENTS

| | | |
|---|---|---|
| 0100056 | 2/1984 | European Pat. Off. . |
| 72533 | 6/1987 | Finland . |
| 946053 | 2/1996 | Finland . |
| 0154713 | 4/1982 | Germany . |
| 2107320A | 4/1983 | United Kingdom . |

OTHER PUBLICATIONS (Abstract) Timonen, M. et al., "Enzymatic cellulose derivative hydrolyzates", EP 382577 A1, Aug. 1990.
(Abstract) McKnight, J.T., "Sausage skin and its manufacture", W. German Patent App. 1 492 643, 1969.
Borchert et al., "Enzymatic Hydrolysis of Cellulosic Materials", Process Biochemistry, pp. 173–180, Dec. (1987).
H. Ruttloff et al., "Industrielle Herstellung und Verwendung von Enzympraparaten", Industrielle Enzyme, pp. 286–297, Edition 1 (1979).

*Primary Examiner*—David A. Redding
*Attorney, Agent, or Firm*—Jones & Askew

[57] ABSTRACT

A method of destruction of sausage skins and other mainly cellulosic substances by means of dissolution with an enzyme solution. Enzymes are added to a reactor that contains a water solution, after or before which the substances to be dissolved are added to the reactor. The substances to be dissolved are dissolved partly or completely, after which a new amount of substances to be dissolved are added to the reactor. When the enzymes have been adsorbed into the new substances to be dissolved, the solution containing the substances dissolved are recovered by separating the solution and the substances to be dissolved from each other, whereby water is added to the substances to be dissolved and if desired, the four foregoing steps are repeated a wished amount of times.

12 Claims, 13 Drawing Sheets

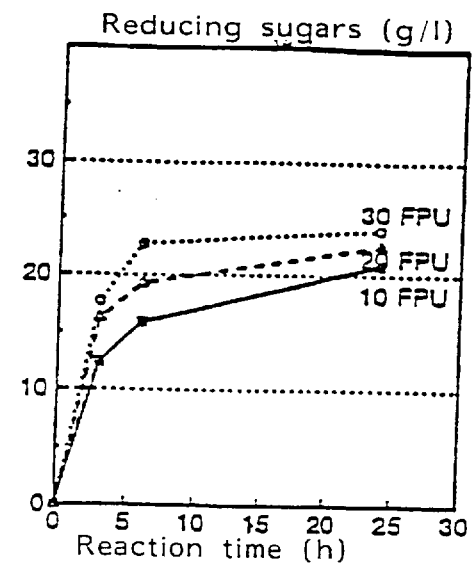
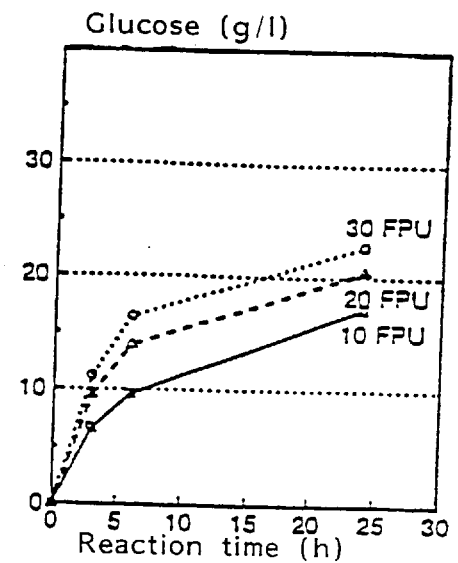
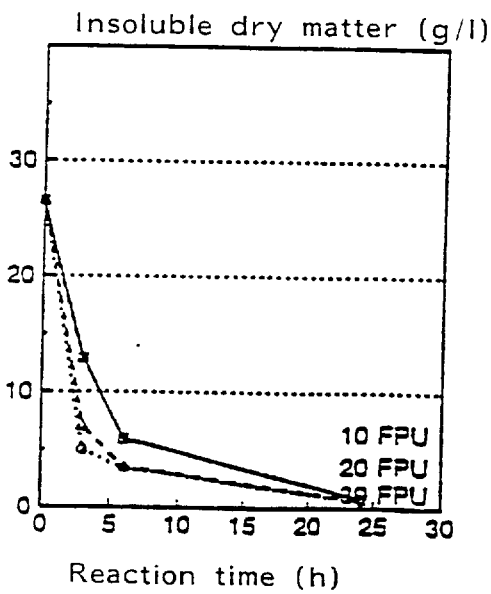
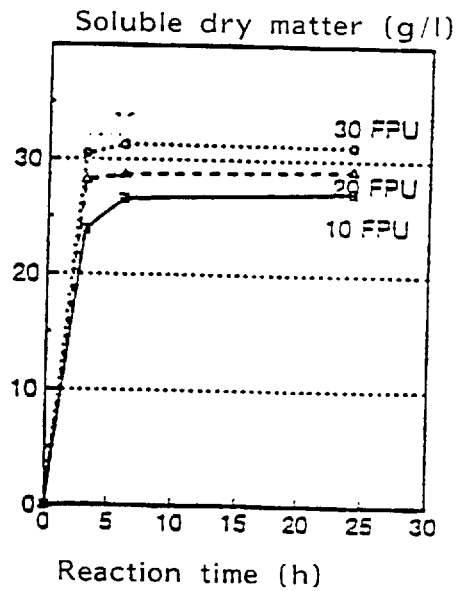
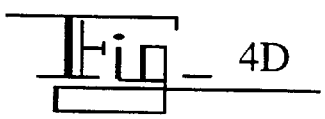

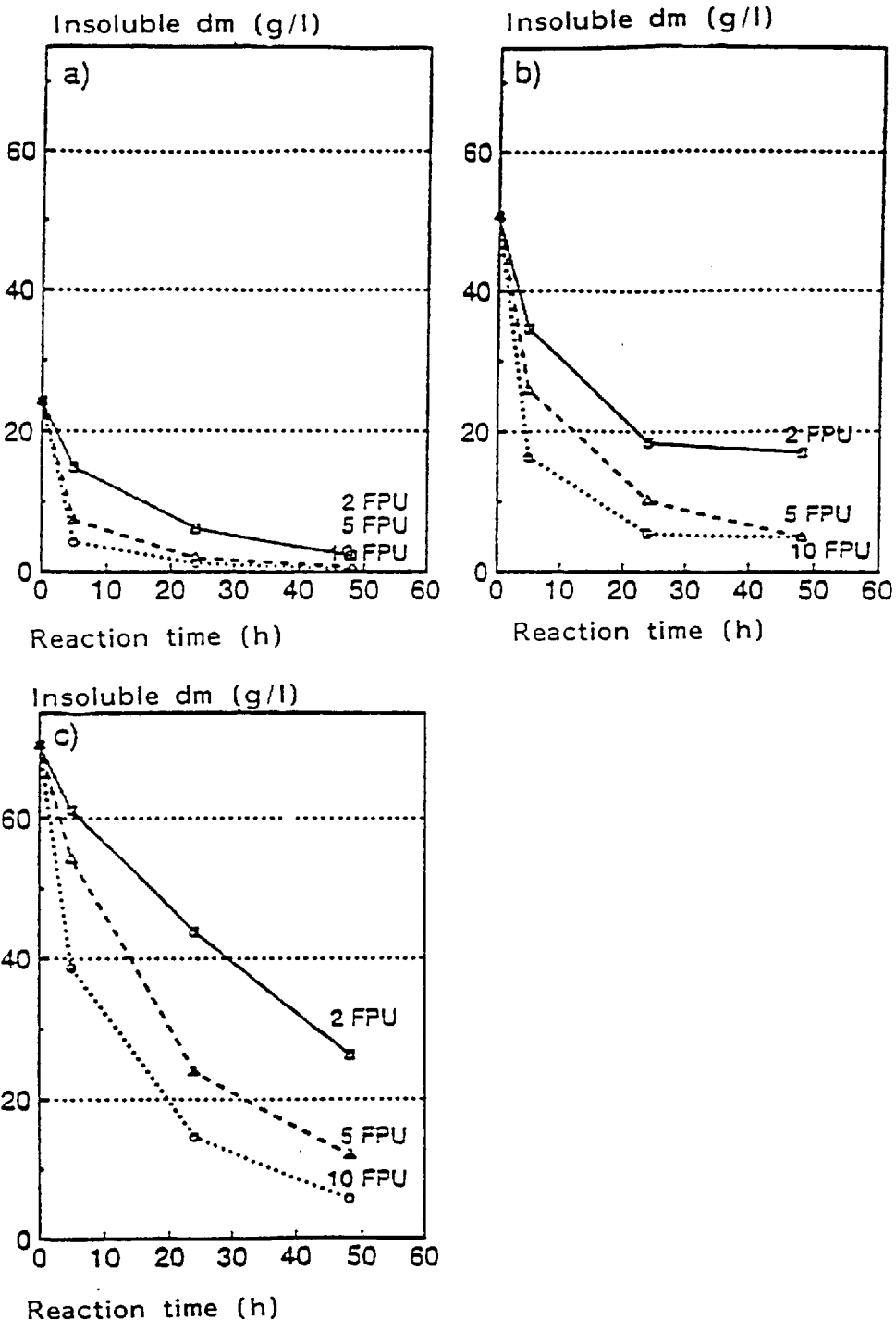

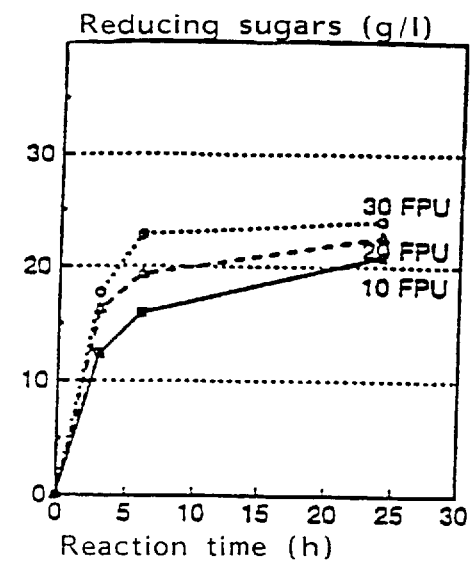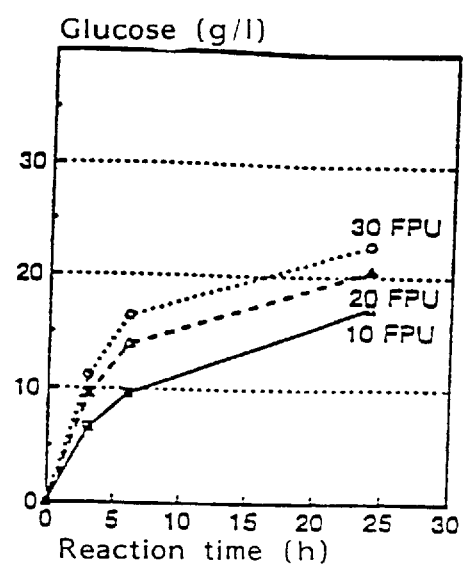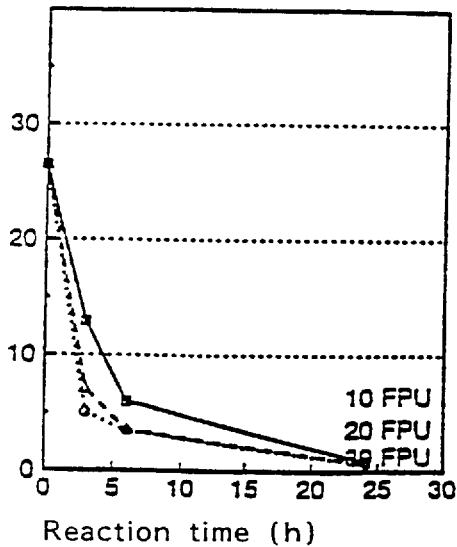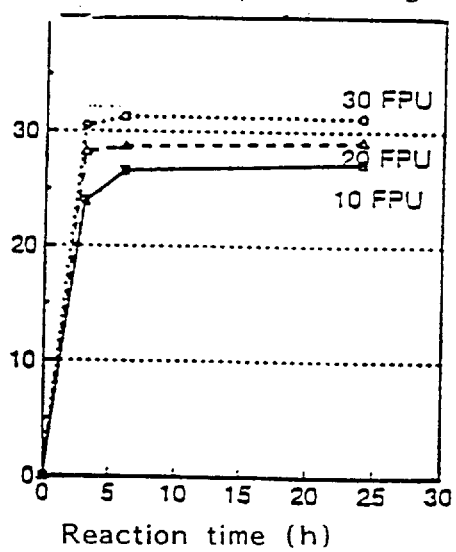

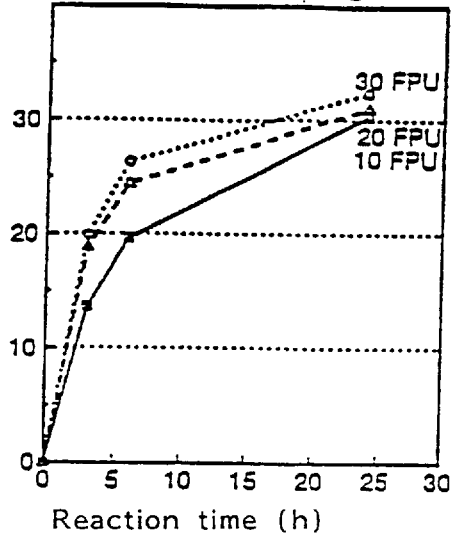
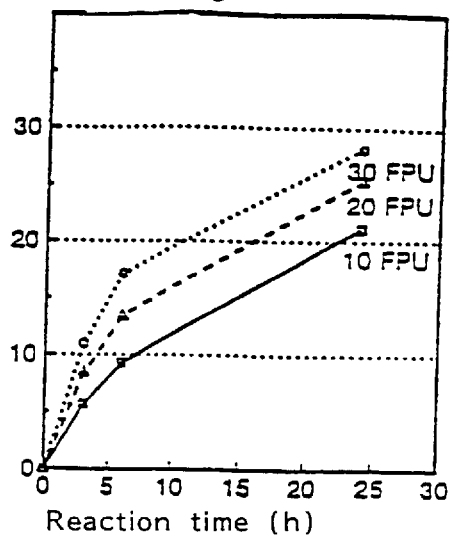
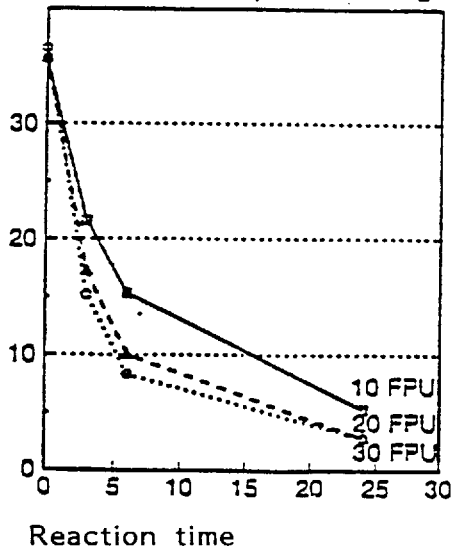
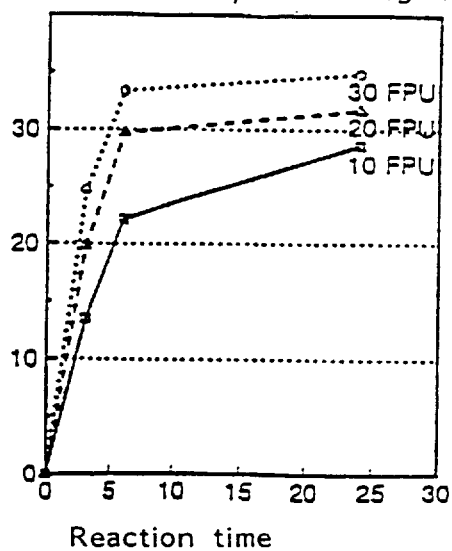

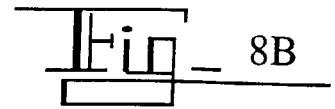
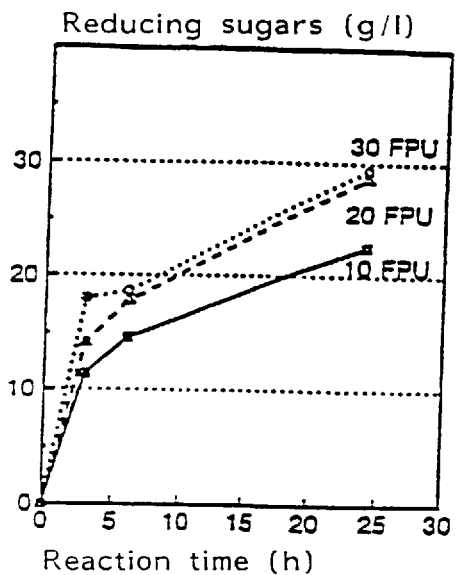
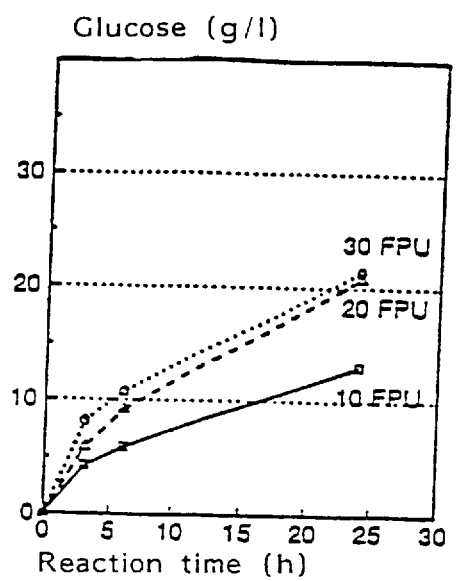
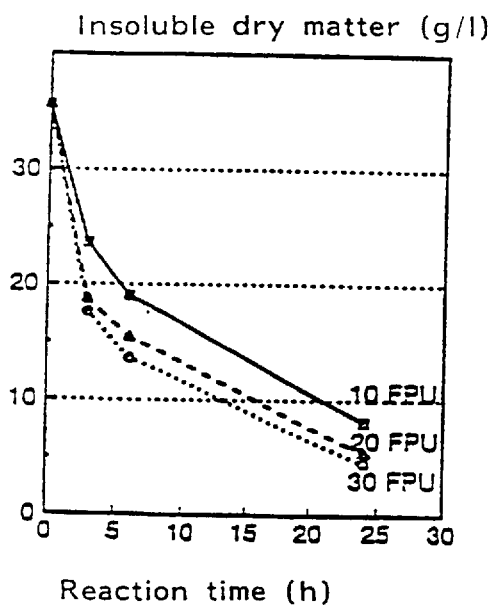
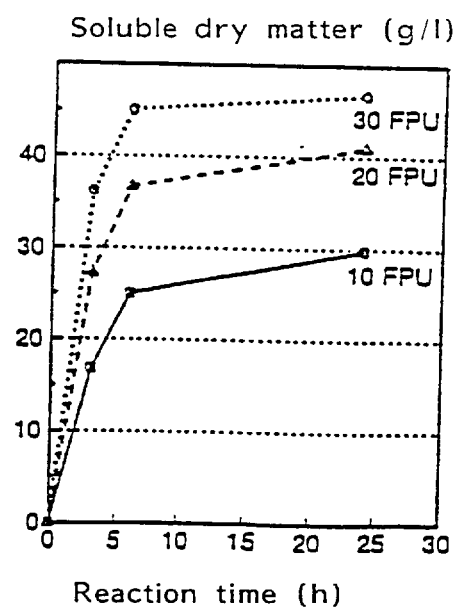
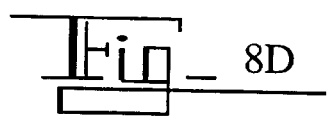

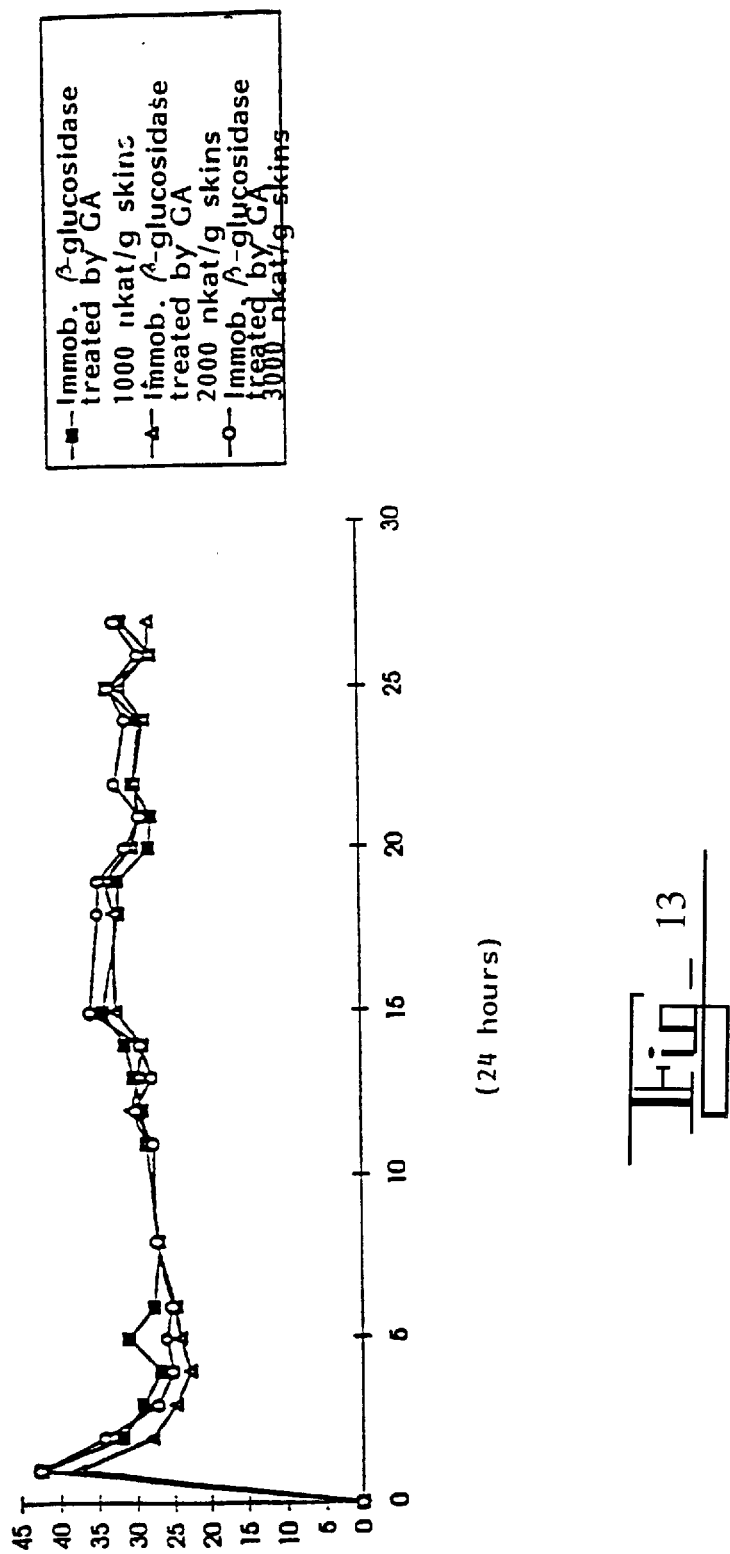

METHOD OF DISSOLUTION OF SAUSAGE SKINS AND OTHER CELLULOSIC SUBSTANCES BY MEANS OF AN ENZYME SOLUTION

FIELD OF THE INVENTION

The invention is concerned with a method of destruction of sausage skins and other mainly cellulose-containing substances by dissolution in an enzyme solution. In this application, the term "sausage skin" means a fibrous casing or a cellulose or CELLOPHANE® casing or some other cellulose-based casing.

BACKGROUND OF THE INVENTION

In sausage factories there is a need to destroy sausage skins because of the large amount of waste they cause. Until now, sausage factories have usually gotten rid of the skins simply by bringing them to the dump. Another usual method is also the composting of sausage skins in wet conditions, which is difficult as different factors, such as the oxygen availability and the temperature, have to be adjusted. One earlier used method is also the burning of sausage skins.

The object of this invention is the destruction of the sausage skins by means of enzyme hydrolysis by an economic method.

SUMMARY OF THE INVENTION

The method of the invention is characterized by the following steps:

a) cellulase enzymes are added to a reactor containing a water solution, b) before step a) or after that, the substances to be dissolved are added to the reactor, c) the substances to be dissolved are allowed to dissolve completely or partially, after which d) a new amount of substances to be dissolved are added to the reactor, and e) when the enzymes have been adsorbed to the new substances to be dissolved, the solution containing the substances, which were dissolved in step c), are recovered by separating the solution and the substances to be dissolved from each other, whereby f) water is added to the substances to be dissolved and if desired, steps c–f are repeated as many times as wished.

Thus, the invention provides an economic method for dissolution of skins by means of enzymes, and as the enzymes are recovered, they are reused in the following dissolution. In practice, there are, however, usually some spillage of the enzymes, and therefore, a given amount of enzymes are preferably added in any stage to the reactor. This amount is, however, little compared with the total amount needed in the hydrolysis.

BRIEF DESCRIPTION OF THE DRAWINGS

FIGS. 4A–4D show the hydrolysis of sausage skins (50 g/l) with an Econase cellulase preparation and the effect of the enzyme administration (10, 20 and 30 FPU/g skin) on the concentration of reducing sugars (FIG. 4A), glucose (FIG. 4B), insoluble dry matter (FIG. 4C), and soluble dry matter (FIG. 4D) as a function of time. Reaction conditions were 50° C., pH 5, mixing at 150 rpm. The size of the skin particles was 3.0×3.0 cm.

FIGS. 5A–5C show the effect of the enzyme and substrate concentrations on the forming of insoluble dry matter as a function of time in the hydrolysis of used sausage skins with an Econase cellulase preparation, with a skin concentration of 50 g/l (FIG. 5A), 100 g/l (FIG. 5B), and 150 g/l (FIG. 5C). Reaction conditions were 50° C., pH 5, mixing at 150 rpm. The size of the skin particles was 3.0×3.0 cm. Enzyme dosage is shown at 2, 5 and 10 FPU/g skins.

FIGS. 6A–6D show hydrolysis of used sausage skins (50 g/l) with an Econase cellulase preparation. The effect of the enzyme dosage (10, 20 and 30 FPU/g skin) on the concentration of reducing sugars (FIG. 6A), glucose (FIG. 6B), insoluble dry matter (FIG. 6C), and soluble dry matter (FIG. 6D) as a function of time. Reaction conditions were 50° C., pH 5, mixing at 150 rpm. The size of the skin particles was 3.0×3.0 cm.

FIGS. 7A–7D show hydrolysis of unused sausage skins (50 g/l) with a Spezyme CE cellulase preparation (Genencor). The effect of the enzyme dosage (10, 20 and 30 FPU/g skin) on the forming of reducing sugars (FIG. 7A), glucose (FIG. 7B), insoluble dry matter (FIG. 7C), and soluble dry matter (FIG. 7D) as a function of time. Reaction conditions were 50° C., pH 5, mixing at 150 rpm. The size of the skin particles was 3.0×3.0 cm.

FIGS. 8A–8D show hydrolysis of unused sausage skins (50 g/l) with a Spezyme CP cellulase preparation (Genencor). The effect of the enzyme dosage (10, 20 and 30 FPU/g skin) on the forming of reducing sugars (FIG. 8A), glucose (FIG. 8B), insoluble dry matter (FIG. 8C), and soluble dry matter (FIG. 8D) as a function of time. Reaction conditions were 50° C., pH 5, mixing at 150 rpm. The size of the skin particles was 3.0×3.0 cm.

FIG. 13 presents the effect of the circulation of the immobilized β-glucosidase on the forming of the soluble dry matter in a semi-continuous hydrolysis of used sausage skins with Econase cellulase. In the beginning there was 50 g/l skins and the enzyme dosage was 30 FPU/g skins. New skins (50 g/l) were added to the reaction mixture every 24 hours. The sugar solution was recovered and substituted with a buffer solution (0.5 FPU/g) containing cellulase. The immobilized β-glucosidase (1000–3000 nkat/g skin) that was treated with glutaraldehyde was added only in the beginning of the reaction. Reaction conditions were 50° C., pH 5, mixing at 150 rpm.

DETAILED DESCRIPTION OF THE INVENTION

Figure 1:
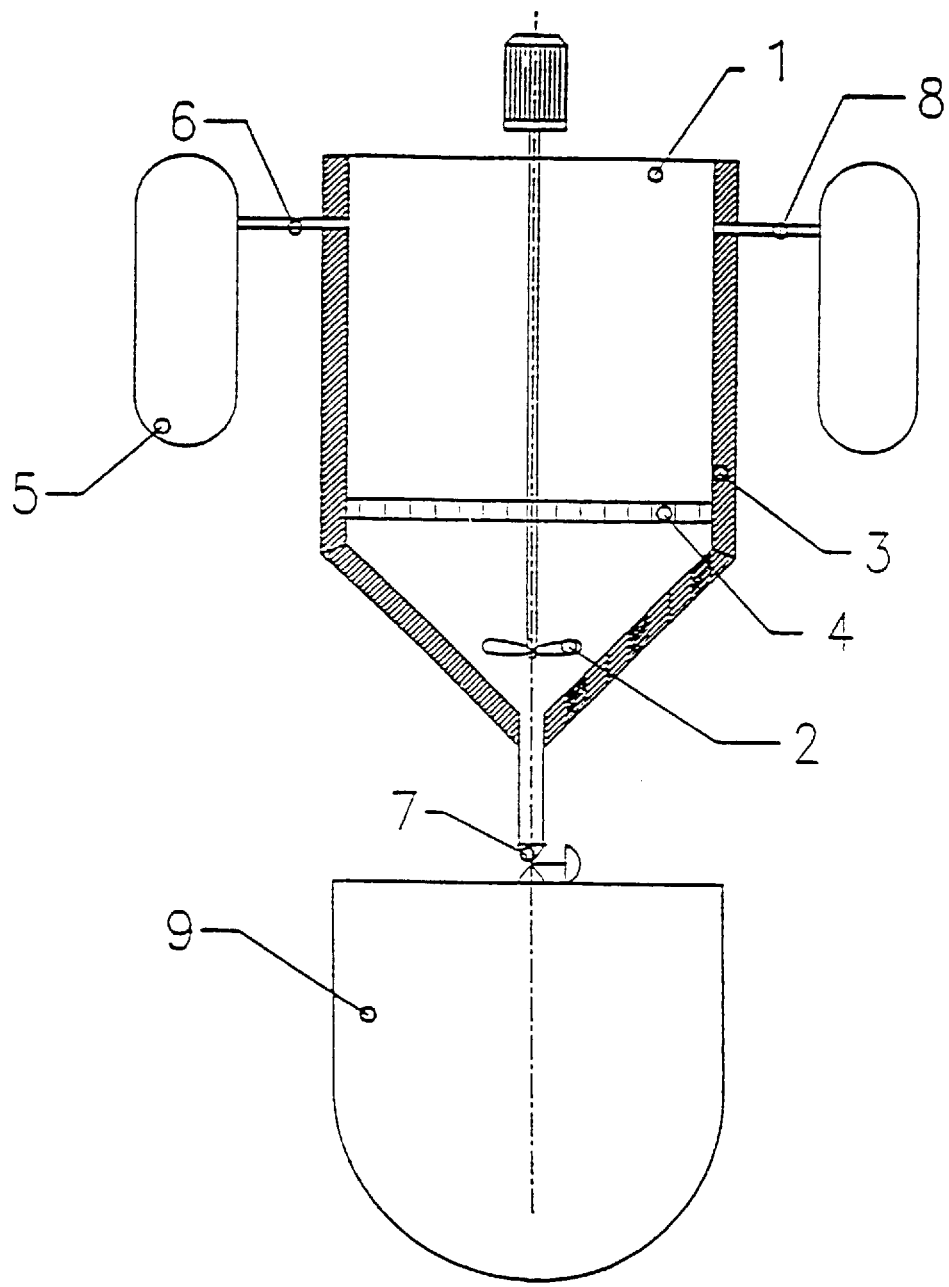
FIG. 1 is a schematic view of the process of the invention.
Figure 2:
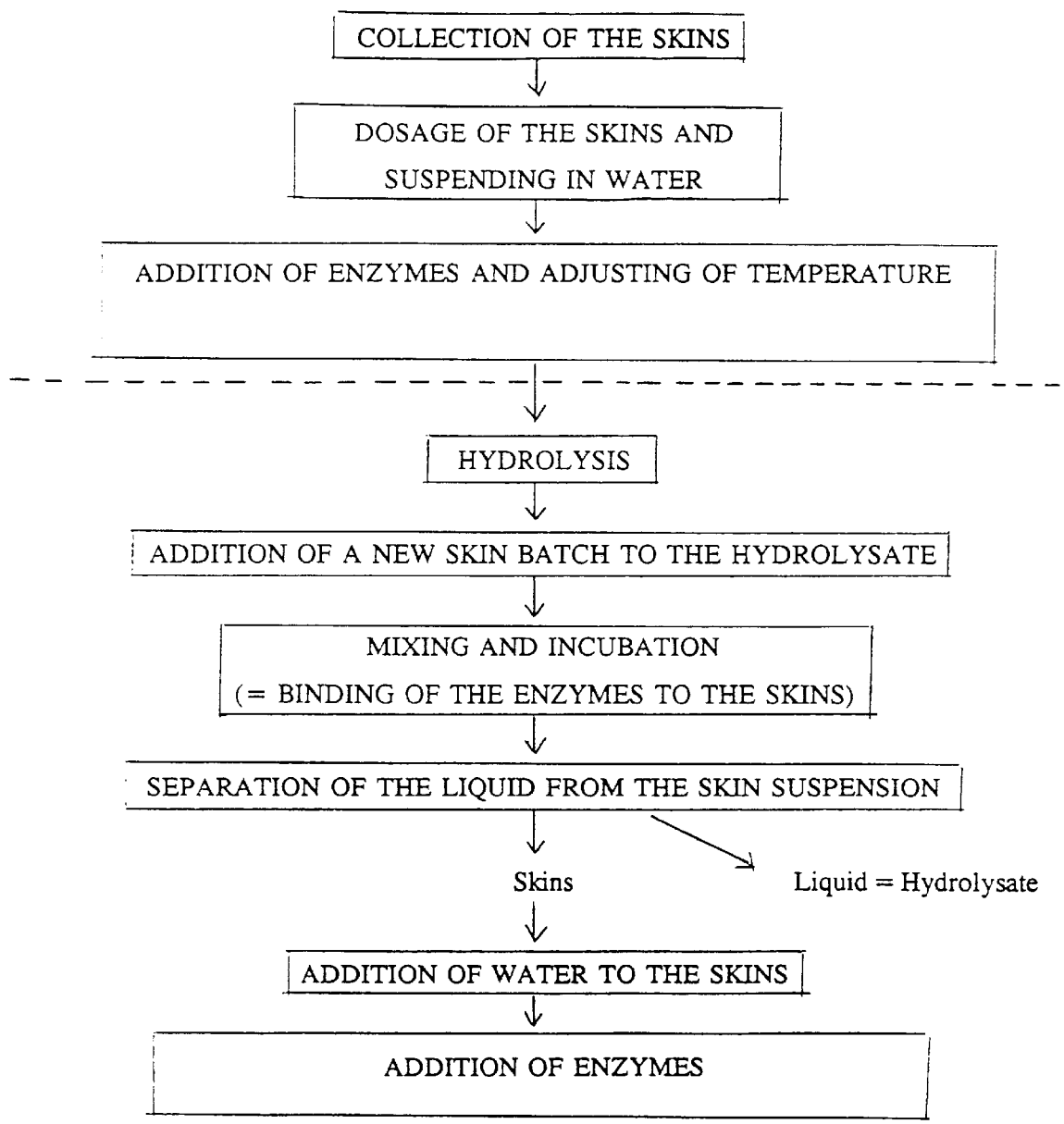
FIG. 2 is a flow diagram of the steps of the method of the invention, wherein the enzyme is circulated.
Figure 3:
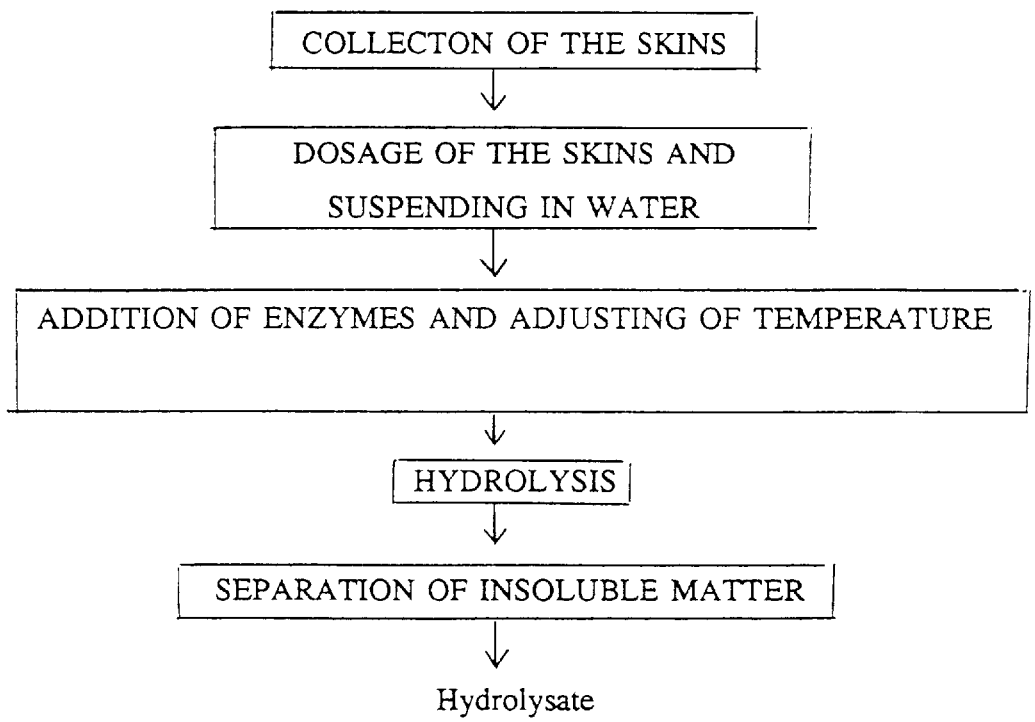
FIG. 3 is a flow diagram of the steps of the method of the invention without any circulation of the enzymes or when the hydrolysis is carried out only once.

In the method of the invention, the skins to be destroyed, and possibly other cellulose-containing substances, are dissolved in a reactor that contains an enzyme solution. The enzymes then adhere to the sausage skin and a hydrolysis reaction for dissolving of these starts. This reaction is continued until a required part of the skins to be dissolved, preferably all of them, have been dissolved, whereafter a new amount of skins to be destroyed is added to the reactor, whereby the enzymes are adsorbed to the new skins. The disintegration products of the skins, in other words the sugars, are in the solution that is recovered from the reactor. These disintegration products, which often simply are measured as reducing sugars, mainly consist of oligo- and monosaccharides, the last mentioned ones mainly of glucose.

In one embodiment of the method, the method can thus be used for example for preparing of glucose, which is obtained as a by-product when the skins are destroyed.

In the method, the destruction of the skins can be followed as a function of time and enzyme and/or skin concentration and/or by defining the concentrations of glucose and reducing sugars and also the amount of insoluble dry matter. The enzymes used are cellulase preparations, preferably commercial and easily available ones, which split up cellulose to hydrocarbons of lower molecular weights than cellulose. The composition of the end product and the proportion of glucose in the dissolved hydrocarbons depend on the ratio of the different activities of the used cellulase preparations.

When the method is simultaneously used for preparing glucose, also β-glucosidase enzyme is preferably added to the reactor, as it produces glucose from cellobiose-disaccharide and oligosaccharides. The β-glucosidase also hinders an inhibition of cellulases because of cellobiose. As β-glucosidase does not adhere to the sausage skins, it is preferably fastened on a solid carrier. The use of such an immobilized β-glucosidase makes it also possible to recirculate this enzyme.

Depending on the concentration of the enzymes and of the skins, the skins can be dissolved in 2–5 hours. In the practice, the time of hydrolysis is chosen by a suitable dose of enzymes, also according to what is preferable in the factory, taking into consideration the costs of the apparatuses, the amount of the skins and the addition of those and also the enzyme costs.

To reduce the enzyme costs, the cellulases are preferably recirculated in a semi-continuous batch hydrolysis so that the enzymes are bound to new skins after the hydrolysis and the recovered sugar solution is preferably substituted with a buffer or water solution for the following hydrolysis. The hydrolysis works for several weeks with the same effect and with only a small substituting enzyme addition. Also an addition of β-glucosidase is needed to keep the hydrolysis level constant, as it does not adhere to the skins, and is thus not reusable. As the β-glucosidase, however, is bound to a solid carrier, the same enzyme batch can be recirculated in several weeks in a semi-continuous hydrolysis without reducing the sugar yields. Thus, the following enzyme consumption can be evaluated from the semi-continuous hydrolysis tests when a new enzyme addition (30 FPU Econase and 100 nkat β-glucosidase/g skin) is carried out every 150th day.

Econase: 0.7 FPU/g skin

Immobilized β-glucosidase: 6.7 nkat/g skin where nkat=nanokatal, a unit of the enzyme activity. One nanokatal produces one nanomole of reaction product in a second, respectively disintegrate or change one nanomole of starting material in a second in conditions to be used in the analysis method.

The need for a completely new enzyme addition depends on many practical factors in the factory. These are, for example, inactivation and enzyme spillage, the deposition of the skins, the hydrolysis time, the fact that the apparatus gets dirty and so on. The reaction product can also be used as fodder.

The invention is described by means of figures. The intention is not to limit the invention to the details of those figures. In the practice there can be used two or several batch reactors 1 in accordance with FIG. 1 (for example 5 m$^3$/500 kg skin/d), wherein the hydrolysis time is for example 24 hours or more. The hydrolysis time can vary depending on the practical function of the factory. The reactors 1 are preferably containers with a mixer 2 and foreseen with mantles 3 (temperature regulation) with a sieve bottom 4 above the mixers. The reactors are supplied from a separate supply/skin collection container 5 along line 6. When the hydrolysis of a given reactor 1 is ready, a new batch of skins are added to the hydrolysate, to which cellulases are adsorbed. When the adsorption is complete, the mixing is stopped and the solution is let through the sieve bottom 4 along line 7 to the production vessel 9. Water is added to the reactor along line 8 and the mixing and the hydrolysis is continued. The immobilized β-glucosidase is kept in the reactor by the sieve 4.

In the alternative, the insoluble dry matter, the skins to which the enzymes are bound and the immobilized β-glucosidase can be separated from the hydrolysate by centrifugation, filtration or other known separation methods of dry matter. The separated insoluble dry matter is returned to the reactor, which in this case is any mixed container with a mantle without any intermediate bottom. The insoluble matters are discharged with desired intervals from the reactor in a suitable stage of the process.

In the following, there are examples with information about the details of the method.

EXAMPLES

INTRODUCTION

Unused and used sausage skins were dissolved enzymatically with three commercial cellulase preparations, with Econase manufactured by Alko and with Spezyme CE- and Spezyme CP-cellulases manufactured by Genencor. The hydrolysis of the skins were observed as a function of time and of the enzyme and the skin content by determining the concentrations of glucose and reducing sugars and the amounts of insoluble and soluble dry matter. To effect the hydrolysis, β-glucosidase enzyme (Novozym 188, Novo) was fastened on a solid carrier.

THE COMPOSITION OF THE SKINS

There was quite much fat (14.9% of dry matter) and proteins in the used skins (10.5% of dry matter). The proportion of insoluble dry matter was smaller and the proportion of soluble dry matter higher than in the unused skins (Table 1).

TABLE 1

The composition of the sausage skins

|  | Unused skins | Used skins |
| --- | --- | --- |
| Dry matter | 80% | 70% |
| Insoluble dry matter | 72% | 53% |
| Soluble dry matter | 8% | 17% |
| Fat | 0.20% of dry matter | 14.9% of dry matter |
| Protein | 0.22 of dry matter | 10.5 of dry matter |

THE ENZYMES USED

In the dissolution tests of the skins, there were used commercial cellulase preparations, in which the activities of the enzymes differed somewhat from each other (Table 2). The cellulase preparations:

Econase CE (Alko)

Spezyme CE (Genencor International)

Spezyme CP (Genencor International)

β-glucosidase:

Novozym 188 (Novo)

The FPU (the hydrolyzing activity on the filter paper) and HEC (the hydroxy ethylcellulose hydrolyzing activity) activities of the cellulase preparations are described as cellulose splitting exo- and endoactivities. The endoglucanases cleave bindings in the cellulose chain by producing oligosaccharides of different sizes and the exoglucanases release cellubiose units from the ends of the chains. β-glucosidase produces glucose from the disaccharides and from the oligosaccharides.

TABLE 2

The activities of the cellulase preparations used

| Activity | Econase | Spezyme CE | Spezyme CP | Novozym |
| --- | --- | --- | --- | --- |
| FPU/Uml | 31 | 49 | 67 | 0.06 |
| HEC nkat/ml | 13500 | 16400 | 23100 | 291 |
| β-glucosidase nkat/ml | 1028 | 450 | 1078 | 7350 |
| β-glucosidase/FPU | 33 | 9 | 16 |  |
| Protein mg/ml | 85 | 109 | 121 | 63 |

BATCH HYDROLYSIS

Reaction conditions

The batch hydrolysis of the sausage skins were made in a water bath (150 rpm) with shaking conical bottles. The whole content of the bottle was taken as a sample from which the sugar and the dry matter contents were determined. The composition of the reaction mixture was:

1.3 g skin as dry matter (50–150 g/l)

19 ml 50 mM acetate buffer, pH 5.0

1 ml enzyme dilution

The enzymes were added according to the FPU activity of the preparations (2–30 FPU/g skin) into the hydrolysis mixtures.

The reactions were made in a dilute buffer in pH 5, as the cellulases work best in slightly acid conditions. It is, however, not necessary to use a buffer as the pH of the water solution of the skins is 5, without any adjusting, and it is not changed during the hydrolysis.

The reaction temperature was 50° C., which is optimal for the function of the cellulases. The temperature can also be lower, for example 30°–50° C. The used skins were hydrolyzed as well as the unused skins.

The fat in the skins remained on the walls of the reaction vessel and on the surface of the liquid. The fat could be cleaved into fatty acids and glycerol by a lipase enzyme that cleave fats, (*Candida cylindracea* lipase, Biocatalysts LTD, UK), but the fatty acids remained suspended in the reaction mixture as they are insoluble in water.

The refining of the skins had no effect on the hydrolysis result. The whole skins (approx. 6×30 cm, 15 g/p) were dissolved with Econase as well as the smaller particles (0.5×0.5 cm; 1×1 cm; 3×3 cm).

Effect of skin and enzyme concentration

The hydrolysis of the sausage skins by Econase cellulase preparation and the effect of the enzyme administration as a function of time are presented in FIG. 4. These results show that the skins are dissolved very well with the method of the invention in approximately 2–5 hours. The insoluble dry matter describes the portion that has not dissolved, and with respect to interpretation of the figure, reference is made to Table 1, wherein there is presented the initial composition of the skins.

In FIG. 5, there has been presented the concentration of insoluble dry matter in the hydrolysis, wherein the contents of the skins (used skins) were 50, 100 and 150 g/l and the cellulase enzyme concentrations (Econase) 2, 5 and 10 FPU/g skin. When a smaller enzyme dose was used (2–5 FPU/g skin) or a bigger concentration of skins (100–150 g/l), a longer reaction time was needed for the maximum hydrolysis. Even if the sugar analysis showed that the hydrolysis was not complete, apparent skins could be seen only in the 5 hour samples and in the 24 hour sample, wherein the skin concentration was 150 g/l and the enzyme concentration 2 FPU/g.

When the enzyme concentration was raised to 30 FPU/g skin, the hydrolysis time shortened to 5 hours (FIG. 6). No skins could be seen even after three hours. There were insoluble dry matter left in an amount of 0.3 g/l.

As the enzyme dose was made according to the FPU activity by using Spezyme-enzymes, the proportion of HEC activity and β-glucosidase remained smaller than with Econase. The skins were dissolved as well as Spezyme enzymes as with the Econase (FIGS. 7 and 8).

SEMI-CONTINUOUS HYDROLYSIS

Figure 9:
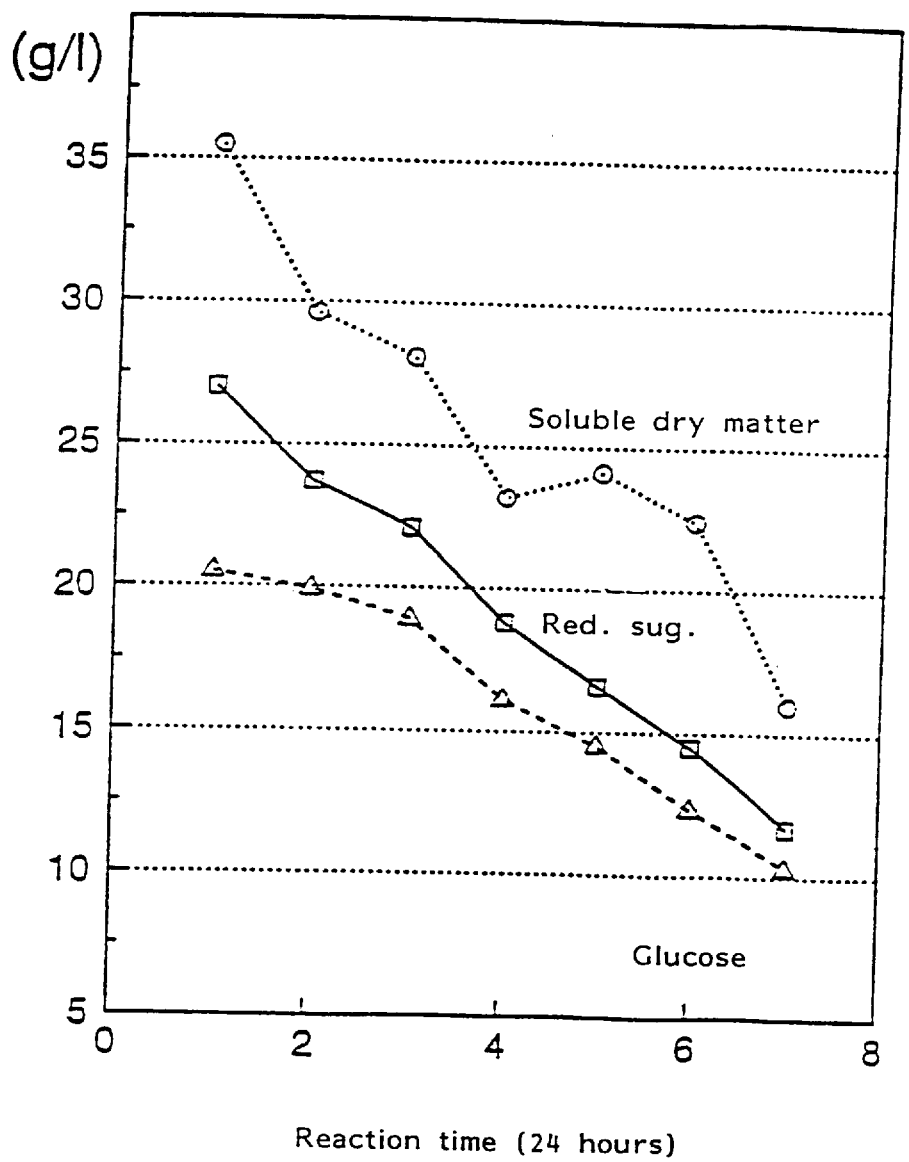
FIG. 9 shows semi-continuous hydrolysis of used sausage skins (50 g/l) with an Econase cellulase preparation (30 FPU/g skin, the size of the skin particles was 3.0×3.0 cm). New skins were added to the reaction mixture every 24 hours. The sugar solution was recovered and substituted with a buffer solution containing β-glucosidase. Reaction conditions were 50° C., pH 5, mixing at 150 rpm.
Figure 10:
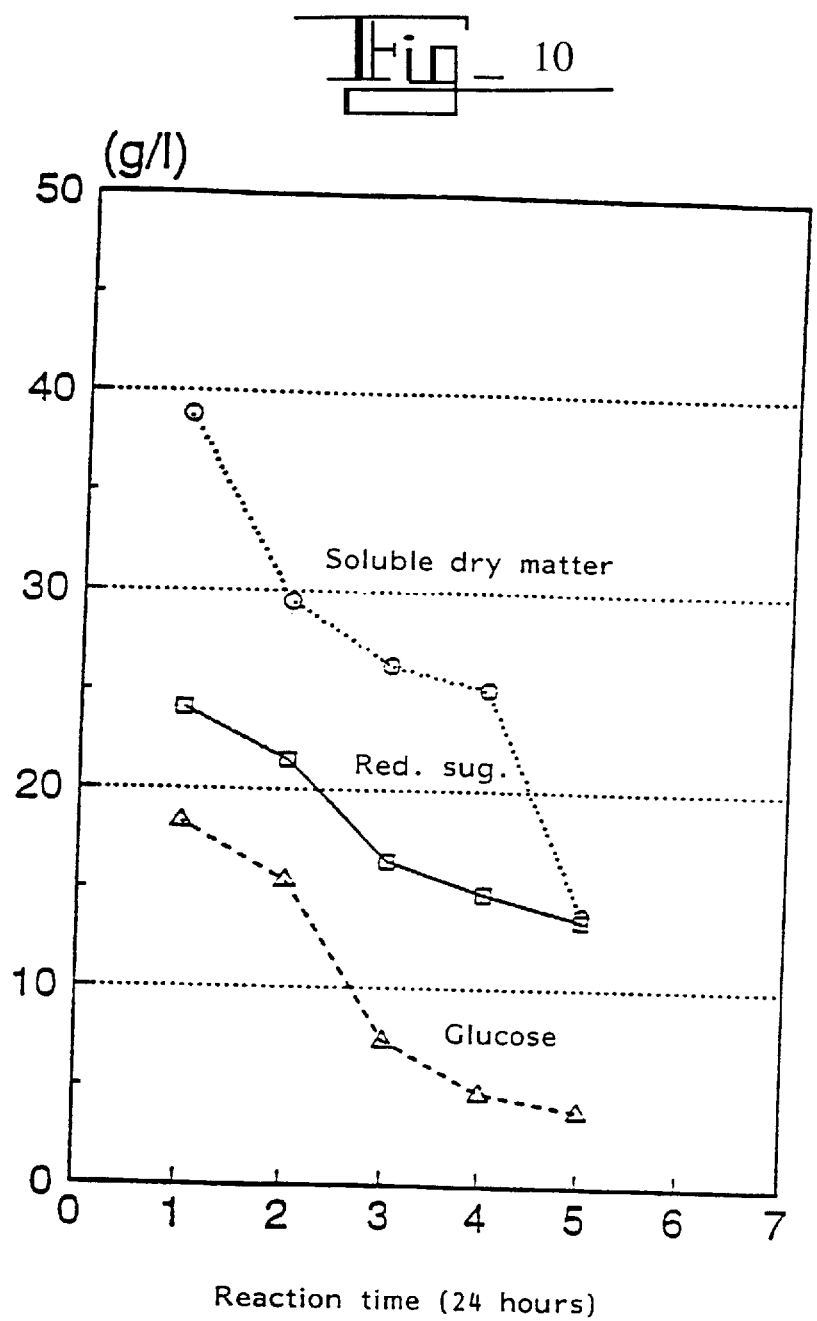
FIG. 10 shows semi-continuous hydrolysis of used sausage skins (50 g/l) with an Econase cellulase preparation (30 FPU/g skin, the size of the skin particles was 3.0×3.0 cm). New skins were added to the reaction mixture every 24 hours. The sugar solution was recovered and substituted with a buffer solution. Reaction conditions were 50° C., pH 5, mixing at 150 rpm.

In a semi-continuous hydrolysis, wherein the enzymes in the sugar solution are recovered after each individual batch hydrolysis, the consumption of the enzymes can be reduced. In a semi-continuous hydrolysis of used skins (50 g/l skin, Econase 30 FPU/g) there were added new skins (50 g/l) in the same reaction mixture after 24 hours hydrolysis, to which the cellulases were allowed to bound in 20 minutes. The binding time was not optimized. The sugar solution was recovered from the skin mixture by centrifugation (2500 rpm, 10 min) and acetate buffer was added instead. It is also possible to recover the skins by filtration. New skins were hydrolyzed again in 24 hours. As the β-glucosidase does not adhere to the cellulose, this enzyme was added in connection with each buffer change in an amount that corresponded to the original β-glucosidase amount (1000 nkat/g skin). The same operation was repeated every 24 hour. The sugar yields were slowly reduced after the second batch hydrolysis because of a small cellulase waste (FIG. 9). Without the β-glucosidase addition the reduction was even faster (FIG.

10). The cellulase was substituted with a little amount of cellulase. Without any substituting cellulase addition, the semi-continuous hydrolysis does not work with the same effect.

To find a suitable stage of adding skins and a suitable hydrolysis time (50 g/l, skins, Econase 10 FPU/g), the skin rests were separated from the skin mixtures after 2, 4, 6 or 24 hours hydrolysis and new skins were added to the solutions. After 24 hours hydrolysis, the solutions were analyzed. The hydrolysis had proceeded best in the reaction mixture wherein the new skins had not been added until 24 hours after the beginning of the hydrolysis (Table 3).

With respect to the hydrolysis it is most preferable that the new skins are not added until the old skins have been completely dissolved and the cellulases have been released to the solution.

TABLE 3

The effect of stage of addition of the skins on the total hydrolysis (24 h)

| Stage of skin addition (h) = hydr. time | Red.sug. (g/l) | Glucose (g/l) | Insoluble dry matter (g/l) | Soluble dry matter (g/l) |
| --- | --- | --- | --- | --- |
| 2 | 7.4 | 4.3 | 15.6 | 47.6 |
| 4 | 9.3 | 4.8 | 7.7 | 51.0 |
| 6 | 16.1 | 8.2 | 5.5 | 52.1 |
| 24 | 22.4 | 15.7 | 1.4 | 55.3 |

Effect of cellulase addition

Figure 11:
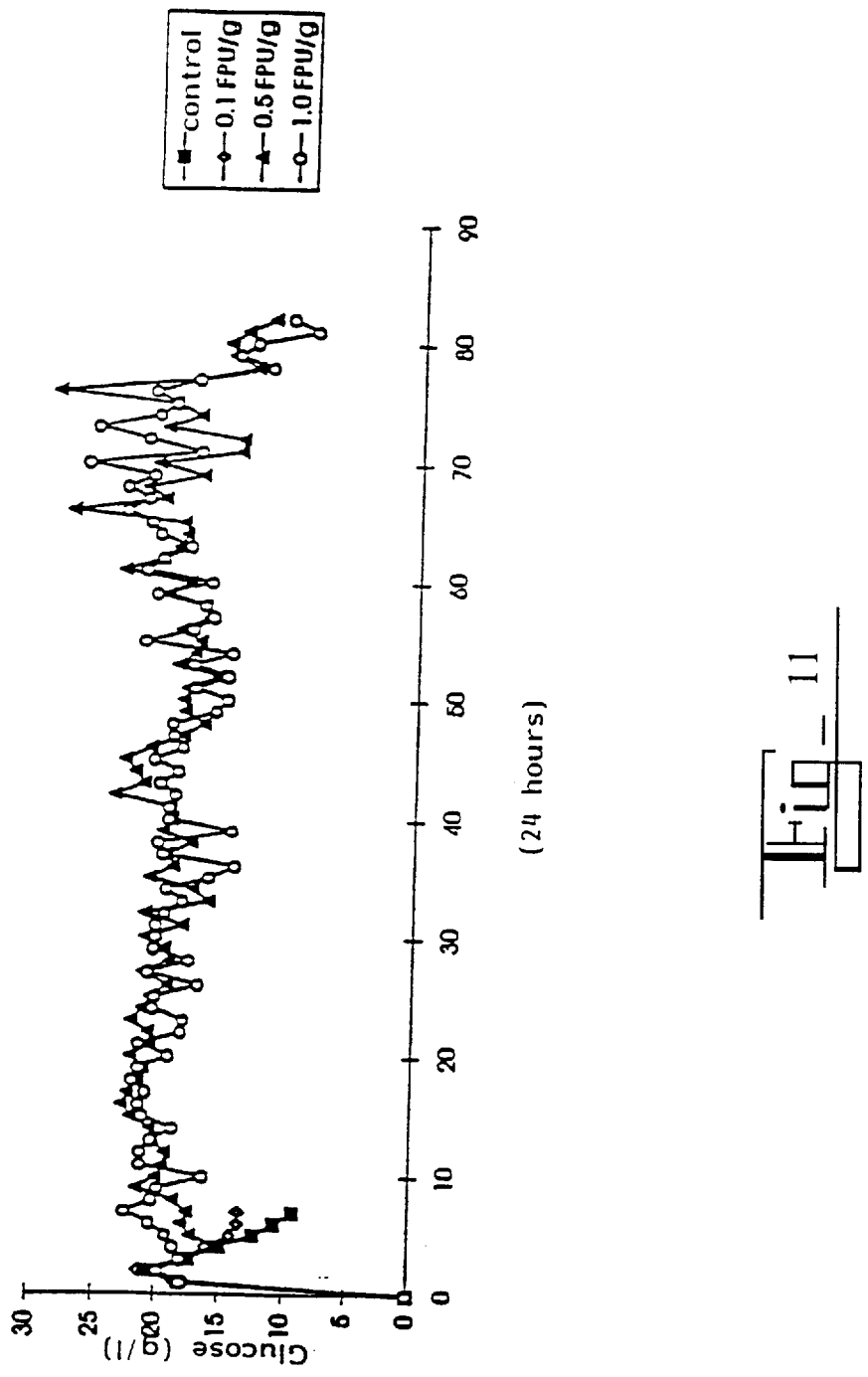
FIG. 11 shows the effect of the cellulase addition on the forming of glucose in a semi-continuous hydrolysis of used sausage skins by Econase cellulase. In the beginning there was 50 g/l skins and the enzyme dosage was 30 FPU/g skins. New skins (50 g/l) were added to the reaction mixture every 24 hours. The sugar solution was recovered and substituted with a buffer solution containing β-glucosidase. Reaction conditions were 50° C., pH 5, mixing at 150 rpm.
Figure 12:
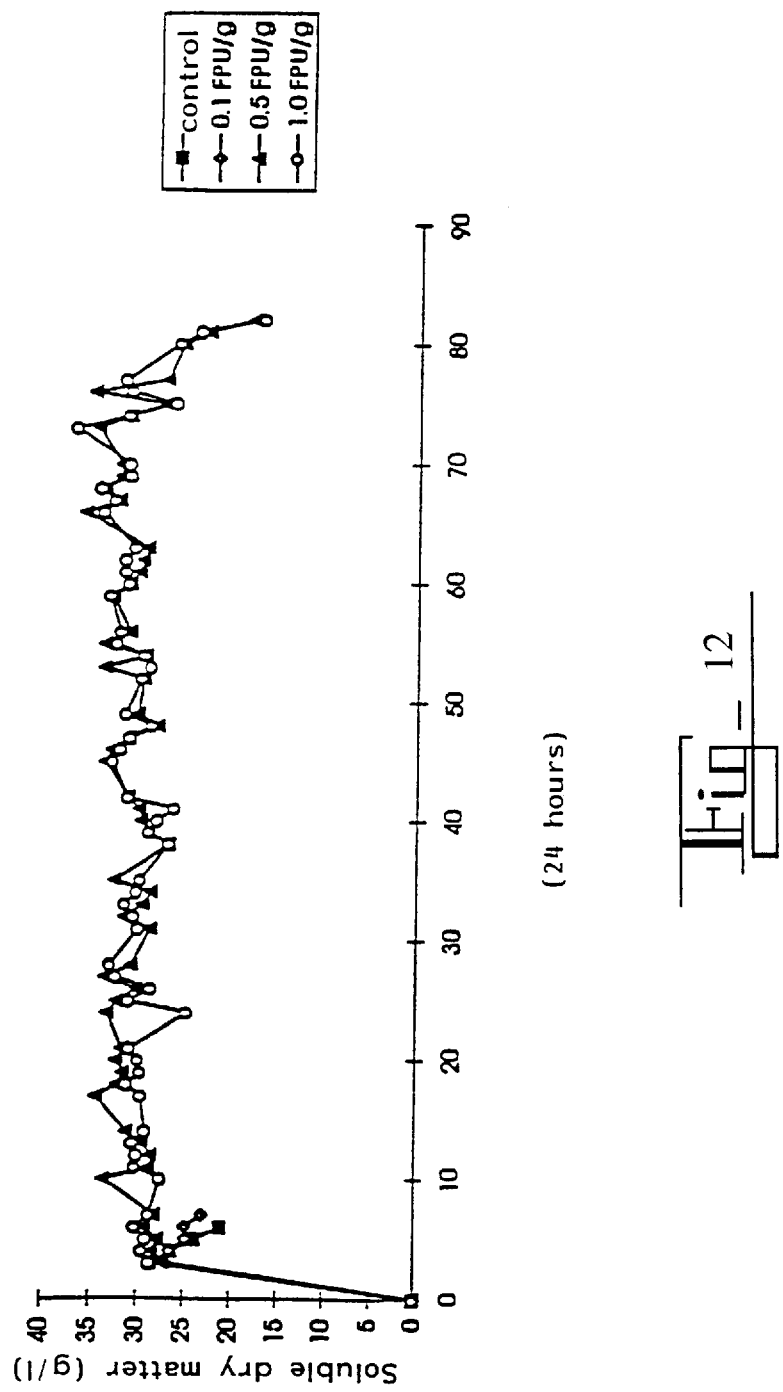
FIG. 12 shows the effect of the cellulase addition on the forming of soluble dry matter in a semi-continuous hydrolysis of used sausage skins by Econase cellulase. In the beginning there was 50 g/l skins and the enzyme dosage was 30 FPU/g skins. New skins (50 g/l) were added to the reaction mixture every 24 hours. The sugar solution was recovered and substituted with a buffer solution containing β-glucosidase (1000 nkat/g) and cellulose. Reaction conditions were 50° C., pH 5, mixing at 150 rpm.

To find a suitable cellulase addition in a semi-continuous hydrolysis there was in addition to the β-glucosidase (1000 nkat/g skin) added Econase 0.1. 0.5 and 1.0 FPU/g skin in connection with each change of the solution. When the enzyme addition was 0.5 or 1.0 FPU/g, the hydrolysis continued for weeks without any reduced sugar yields. The glucose concentration was in average 22 g/l (63% of dry matter), the concentration of all reducing sugars 25 g/l (71% of dry matter) and the soluble dry matter 33 g/l. The hydrolysis was stopped after 78 days (FIGS. 11 and 12). During this time there was not any growth of the microorganisms or depositing of fat in the hydrolysis vessel.

The real enzyme consumption in a hydrolysis, wherein the enzymes are circulated, can be calculated from the results:

The initial addition of cellulase of 30 FPU/g skin to one batch every 150th day.

The addition of cellulase of 0.5 FPU/g skin to each batch and the addition of β-glucosidase of 1000 nkat/g skin to each batch.

TOTAL: 0.7 FPU Econase and 1000 nkat β-glucosidase/g skin.

The immobilization of β-glucosidase in a solid carrier

An addition of soluble β-glucosidase continuously to the hydrolysis mixture increases the enzyme costs considerably. As there is no commercial β-glucosidase that is bound to a solid carrier suitable for continuous use, this immobilized enzyme preparation was prepared.

The binding of Novo β-glucosidase was studied with five different carriers. The immobilization mixture contained 5 g carrier washed with water, 49 ml 50 mM acetate buffer, pH 5 and 1.35 ml enzyme (2000 nkat/g carrier). The reaction mixtures were agitated slightly in cold conditions (+4° C.) for 24 hours. The binding of the enzyme was followed from the solutions and the carriers. The β-glucosidase was best bound to a weak cation exchanger. The enzyme was fastened with glutaraldehyde by cross-linking to improve the stability of the carrier.

Immobilized β-glucosidase (1000 nkat/g skin) was circulated in a semi-continuous hydrolysis of sausage skins in three weeks, whereby it worked as a soluble enzyme. Without any glutaraldehyde binding, the enzyme was released quite quickly from the carrier. Also three different amounts of glutaraldehyde treated immobilized β-glucosidase (1000, 2000 and 3000 nkat/g skin) was circulated during a month in the hydrolysis without any reduction of the sugar yields.

In FIG. 13 there has been presented the effect of the circulation of the immobilized β-glucosidase on the forming of the soluble dry matter in a semi-continuous hydrolysis of used sausage skins with Econase cellulase. In the beginning there was 50 g/l skins and the enzyme dose was 30 FPU/g skins. Every 24 hour there had been added new skins to the reaction mixture (50 g/l), the sugar solution was recovered and substituted with a buffer solution containing cellulase (0.5 FPU/g). The immobilized β-glucosidase that was treated with glutaraldehyde (1000–3000 nkat/g skin) was added only in the beginning of the reaction. The reaction conditions: 50° C., pH 5, mixing 150 rpm.

The enzyme costs can be reduced by using an immobilized β-glucosidase. The same enzyme batch can be circulated for several weeks or months in a continuous hydrolysis.

We claim:

1. Method of destruction of sausage skins and other mainly cellulosic substances by means of dissolution with an enzyme solution, comprising the following steps:

a) adding cellulase enzymes to a reactor containing a water solution;

b) adding the substances to be dissolved to the reactor, either before or after adding the cellulose enzymes;

c) dissolving the substances to be dissolved partly or completely, and then;

d) adding to the reactor a new amount of substances to be dissolved;

e) when the enzymes have been absorbed in the new substances to be dissolved, resolving the solution containing the described substances by separating the solution and the substances to be dissolved from each other, whereby f) water is added to the substances to be dissolved and if desired, steps c–f are repeated a wished amount of times.

2. Method of claim 1, characterized in that the enzymes are cellulases.

3. Method of claim 1, characterized in that the cellulase preparations are at least one of Econase CE, Spezyme CE and Spezyme CP.

4. Method of claim 1, characterized in that the hydrolysis time is adjusted by the concentration of the skins and the concentration of the enzyme.

5. Method of claim 1, characterized in that the hydrolysis time is 2–5 hours when the concentration of the skins is ca 0–100 g/l and the concentration of the enzymes 1–50 FPU/g skins.

6. Method of claim 1, characterized in that the amount of cellulase enzyme in the solution is 1–50 FPU/g skin.

7. Method claim 1, characterized in that also β-glucosidase is added to the process for effecting the hydrolysis when a bigger amount of glucose is desired.

8. Method of claim 7, characterized in that the β-glucosidase is immobilised for recirculating of the same.

9. Method of claim 8, characterized in that the amount of immoblised β-glucosidase is ca 1000 nkat/g skins.

10. Method of claim 7, characterized in that between the additions of the skins or in connection with those, the needed amount of cellulase enzymes and β-glucosidase is added.

11. Method of claim 1, characterized in that the skin concentration is 10/200 g/l.

12. Method of claim 1, characterized in that the method is carried out as a semi-continuous batch process by using one, two or several reactors.

* * * * *